(12) United States Patent
Petzoldt et al.

(10) Patent No.: US 7,015,354 B2
(45) Date of Patent: Mar. 21, 2006

(54) PREPARATION OF (METH)ACROLEIN AND/OR (METH)ACRYLIC ACID

(75) Inventors: Jochen Petzoldt, Weisenheim am Berg (DE); Signe Unverricht, Mannheim (DE); Heiko Arnold, Nanjing (CN); Klaus Joachim Müller-Engel, Stutensee (DE); Martin Dieterle, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/917,414

(22) Filed: Aug. 13, 2004

(65) Prior Publication Data

US 2005/0038291 A1    Feb. 17, 2005

Related U.S. Application Data

(60) Provisional application No. 60/494,814, filed on Aug. 14, 2003.

(30) Foreign Application Priority Data

Aug. 14, 2003  (DE)  ................................ 103 37 788

(51) Int. Cl.
    *C07C 51/16*   (2006.01)
    *C07C 45/00*   (2006.01)

(52) U.S. Cl. ...................................... 562/547; 568/479
(58) Field of Classification Search ............ None
    See application file for complete search history.

(56) References Cited

U.S. PATENT DOCUMENTS

| | | |
|---|---|---|
| 3,147,084 A | 9/1964 | Franzen et al. |
| 3,775,474 A | 11/1973 | Ohara et al. |
| 3,871,445 A | 3/1975 | Wanka et al. |
| 3,893,951 A | 7/1975 | Grasselli et al. |
| 3,954,855 A | 5/1976 | Wada et al. |
| 4,259,211 A | 3/1981 | Krabetz et al. |
| 4,294,873 A | 10/1981 | Hartmann et al. |
| 4,297,247 A | 10/1981 | Krabetz et al. |
| 4,298,763 A | 11/1981 | Engelbach et al. |
| 4,339,355 A | 7/1982 | Decker et al. |
| 4,438,217 A | 3/1984 | Takata et al. |
| 4,537,874 A | 8/1985 | Sato et al. |
| 5,144,091 A | 9/1992 | Martan et al. |
| 5,364,825 A | 11/1994 | Neumann et al. |
| 5,446,004 A | 8/1995 | Tenten et al. |
| 5,449,821 A | 9/1995 | Neumann et al. |
| 5,493,052 A | 2/1996 | Tenten et al. |
| 5,521,137 A | 5/1996 | Martin et al. |
| 5,637,546 A | 6/1997 | Tenten et al. |
| 5,677,261 A | 10/1997 | Tenten et al. |
| 5,686,373 A | 11/1997 | Tenten et al. |
| 5,739,391 A | 4/1998 | Ruppel et al. |
| 5,821,390 A | 10/1998 | Ruppel et al. |
| 5,885,922 A | 3/1999 | Hibst et al. |
| 5,910,608 A | 6/1999 | Tenten et al. |
| 6,028,220 A | 2/2000 | Wada et al. |
| 6,124,499 A | 9/2000 | Hibst et al. |
| 6,169,214 B1 | 1/2001 | Tenten et al. |
| 6,383,976 B1 | 5/2002 | Arnold et al. |
| 6,395,936 B1 | 5/2002 | Arnold et al. |
| 6,403,829 B1 | 6/2002 | Unverricht et al. |
| 6,410,785 B1 | 6/2002 | Zehner et al. |
| 6,525,217 B1 | 2/2003 | Unverricht et al. |
| 6,541,664 B1 | 4/2003 | Jachow et al. |
| 2004/0015012 A1 | 1/2004 | Hammon et al. |
| 2004/0062870 A1 | 4/2004 | Dieterle et al. |
| 2004/0097368 A1 | 5/2004 | Borgmeier et al. |
| 2004/0138500 A1 | 7/2004 | Borgmeier |
| 2004/0171874 A1 | 9/2004 | Watanabe et al. |
| 2004/0182190 A1 | 9/2004 | Murakami et al. |
| 2004/0191953 A1 | 9/2004 | Dieterle et al. |

FOREIGN PATENT DOCUMENTS

| | | |
|---|---|---|
| DE | 2 201 528 | 11/1972 |
| DE | 25 13 405 | 10/1976 |
| DE | 26 26 887 | 12/1977 |
| DE | 28 30 765 | 1/1980 |
| DE | 29 03 218 | 8/1980 |
| DE | 29 03 582 | 8/1980 |
| DE | 29 09 671 | 10/1980 |
| DE | 31 51 805 | 7/1983 |
| DE | 33 00 044 | 7/1983 |
| DE | 33 38 380 | 4/1984 |
| DE | 40 23 239 | 1/1992 |
| DE | 43 02 991 | 8/1994 |
| DE | 43 35 973 | 4/1995 |
| DE | 195 28 646 | 2/1997 |
| DE | 197 36 105 | 2/1999 |
| DE | 197 46 210 | 4/1999 |
| DE | 198 55 913 | 6/2000 |
| DE | 199 02 562 | 7/2000 |
| DE | 199 48 248 | 4/2001 |
| DE | 199 48 523 | 4/2001 |
| DE | 100 29 338 | 1/2002 |
| DE | 100 33 121 | 1/2002 |
| DE | 100 34 825 | 1/2002 |
| DE | 101 22 027 | 5/2002 |

(Continued)

*Primary Examiner*—Paul A. Zucker
(74) *Attorney, Agent, or Firm*—Oblon, Spivak, McClelland, Maier & Neustadt, P.C.

(57) ABSTRACT

A process for preparing (meth)acrolein and/or (meth)acrylic acid by heterogeneously catalyzed gas phase partial oxidation of an organic precursor compound over a fresh fixed catalyst bed, in which the process is started up at a reduced hourly space velocity of charging gas mixture on the fixed catalyst bed.

4 Claims, No Drawings

FOREIGN PATENT DOCUMENTS

| | | |
|---|---|---|
| DE | 102 32 482 | 1/2004 |
| DE | 102 54 278 | 2/2004 |
| DE | 103 13 209 | 3/2004 |
| DE | 102 48 584 | 4/2004 |
| DE | 102 54 279 | 6/2004 |
| DE | 102 61 186 | 7/2004 |
| EP | 0 015 565 | 9/1980 |
| EP | 0 034 442 A2 | 8/1981 |
| EP | 0 279 374 | 8/1988 |
| EP | 0 293 224 | 11/1988 |
| EP | 0 293 859 | 12/1988 |
| EP | 0 383 224 | 8/1990 |
| EP | 0 427 508 | 5/1991 |
| EP | 0 450 596 A2 | 10/1991 |
| EP | 0 575 897 | 12/1993 |
| EP | 0 668 103 | 8/1995 |
| EP | 0 668 104 | 8/1995 |
| EP | 0 700 714 | 3/1996 |
| EP | 0 700 893 | 3/1996 |
| EP | 0 714 700 | 6/1996 |
| EP | 0 807 465 | 11/1997 |
| EP | 0 962 253 | 12/1999 |
| EP | 0 990 636 | 4/2000 |
| EP | 1 106 598 | 6/2001 |
| EP | 1 180 508 | 2/2002 |
| EP | 1 192 987 | 4/2002 |
| EP | 1 260 495 | 11/2002 |
| WO | WO 98/24746 | 6/1998 |
| WO | WO 00/53556 | 9/2000 |
| WO | WO 00/53557 | 9/2000 |
| WO | WO 00/53558 | 9/2000 |
| WO | WO 00/53559 | 9/2000 |
| WO | WO 02/098827 | 12/2002 |

# PREPARATION OF (METH)ACROLEIN AND/OR (METH)ACRYLIC ACID

The present invention relates to a process for preparing (meth)acrolein and/or (meth)acrylic acid by heterogeneously catalyzed gas phase partial oxidation by charging a fresh fixed catalyst bed disposed in a reactor at elevated temperature with a charging gas mixture which, in addition to at least one organic precursor compound to be partially oxidized and molecular oxygen as an oxidant, comprises at least one diluent gas which behaves substantially inertly under the conditions of the heterogeneously catalyzed gas phase partial oxidation.

In this document, the notation (meth)acrolein is an abbreviation of methacrolein or acrolein.

In this document, (meth)acrylic acid is an abbreviation of methacrylic acid or acrylic acid.

(Meth)acrolein and (meth)acrylic acid are reactive monomers which are suitable, for example, for preparing polymers which may find use, inter alia, as adhesives.

On the industrial scale, (meth)acrolein and (meth)acrylic acid are prepared predominantly by heterogeneously catalyzed gas phase partial oxidation of suitable $C_3/C_4$ precursor compounds, in particular of propene and propane in the case of acrolein and acrylic acid, or of isobutene and isobutane in the case of methacrylic acid and of methacrolein. However, also suitable as starting materials in addition to propene, propane, isobutene and isobutane are other compounds containing 3 or 4 carbon atoms, for example isobutanol, n-propanol or the methyl ether (as a precursor of a $C_4$ precursor) of isobutanol. (Meth)acrylic acid can also be obtained from (meth)acrolein.

The catalysts to be used for such gas phase partial oxidations are normally solid state multielement oxides.

The heterogeneously catalyzed gas phase partial oxidation of $C_3/C_4$ precursors to (meth)acrolein and/or (meth)acrylic acid is typically carried out by charging a fixed catalyst bed at elevated temperature with a charging mixture which, in addition to the at least one organic precursor compound to be partially oxidized, comprises molecular oxygen as an oxidant.

The fixed catalyst bed is normally surrounded by a jacket (for example it may be disposed in the catalyst tubes of a tube bundle reactor). On this side of the jacket, the exothermic partial oxidation takes place during the residence time on the catalyst surface, and, on the other side of the jacket, a heat carrier (for example a salt bath) is conducted, in order to absorb and remove the heat of reaction.

In addition, the reaction partners are generally diluted with a gas which is substantially inert under the conditions of the gas phase partial oxidation and, with its heat capacity, is capable of absorbing heat of reaction which is released additionally and, in most cases, is capable of simultaneously favorably influencing the explosion behavior of the charging gas mixture. In addition, it typically exerts an advantageous influence on the reaction rate. Typically, the inert diluent gases used are noncombustible gases.

One of the most frequently used inert diluent gases is molecular nitrogen which is always automatically used when the oxygen source for the heterogeneously catalyzed gas phase partial oxidation is air.

As a consequence of its general availability, another diluent gas which is used in many cases is steam. In many cases, cycle gas is also used as an inert diluent gas (cf., for example, EP-A 1180508). Cycle gas refers to the residual gas which remains in the heterogeneously catalyzed gas phase partial oxidation of the at least one organic precursor compound when the target product ((meth)acrolein and/or (meth)acrylic acid) is removed more or less selectively (for example by absorption into a suitable solvent) from the product gas mixture. In general, it consists predominantly of the inert diluent gases used for the heterogeneously catalyzed gas phase partial oxidation, and also of the steam typically by-produced in the course of the gas phase partial oxidation and of carbon oxides formed by undesired full secondary oxidation. It sometimes contains small amounts of oxygen which has not been consumed in the gas phase partial oxidation (residual oxygen) and/or of unconverted organic starting compounds. Typically, only a portion of the residual gas is used as cycle gas. The remaining amount of residual gas is generally incinerated.

Depending on the catalyst charge and reaction conditions selected, the gas phase partial oxidation of the precursor compound may lead predominantly to (meth)acrolein, or to a mixture of (meth)acrolein and (meth)acrylic acid, or predominantly to (meth)acrylic acid.

The reason for this is that the gas phase partial oxidation of suitable $C_3/C_4$ precursor compounds to (meth)acrylic acid normally proceeds in two successive steps. The first step leads to (meth)acrolein and the second step to (meth)acrylic acid.

In general, the two steps are carried out over different catalyst charges arranged in spatial succession, and the individual catalyst charge is tailored to the particular reaction step to be catalyzed. This is then also referred to as a multistage gas phase partial oxidation. In the first stage, predominantly (meth)acrolein is formed. The product gas mixture leaving the first stage is subsequently, optionally after intermediate cooling and/or supplementation of molecular oxygen (for example in the form of air), conducted directly into the second stage, where (meth)acrolein formed in the first stage is further oxidized to (meth)acrylic acid.

The temperature in the particular reaction stage is normally likewise adjusted to the optimum of the particular reaction step.

It is appropriate from an application point of view to realize the particular reaction stage in a dedicated reactor (for example in a tube bundle reactor) (cf., for example, EP-A 700 893 and EP-A 700 714).

However, both reaction stages can also be carried out in a single reactor which then generally has more than one temperature zone (cf., for example, EP-A 1 106 598 and EP-A 990 636).

However, multielement oxide active compositions are also known which are capable of catalyzing more than only one step (cf., for example, EP-A 962 253, EP-A 1 260 495, DE-A 10 122 027, EP-A 1 192 987 and EP-A 962 253).

In such cases, depending on the selected reaction conditions in a reaction stage, it is possible either to obtain substantially only (meth)acrolein, or a mixture of (meth)acrolein and (meth)acrylic acid, or substantially only (meth)acrylic acid. Normally, such a reaction stage is realized in a reactor.

However, it will be appreciated that a single reaction step can also be carried out in a reactor which, to improve the target product selectivity, has more than one temperature zone, as recommended, for example, in EP-A 1 106 598, in WO 00/53556, in WO 00/53559, in WO 00/53557 and in WO 00/53558.

To prepare (meth)acrolein and/or (meth)acrylic acid by a process for heterogeneously catalyzed gas phase partial oxidation, a starting reaction gas mixture comprising at least one precursor compound to be partially oxidized, molecular oxygen as an oxidant and at least one diluent gas which behaves substantially inertly under the conditions of the heterogeneously catalyzed gas phase partial oxidation (the charging gas mixture) is therefore normally conducted through a fixed catalyst bed charge at elevated temperature (generally a few hundred ° C., typically from 100 to 600° C.). The chemical conversion proceeds during the contact time on the catalyst surface and the heat of reaction is passed to a flowing heat exchanger in particular by indirect heat exchange.

A disadvantage of a heterogeneously catalyzed gas phase partial oxidation carried out in this way is that the heat of reaction has to be removed on the one hand at a sufficient rate to prevent overheating of the system. On the other hand, the heat removal must not be too fast, since the reaction otherwise in some cases ceases. Conversely, the reaction, especially at the beginning, has to develop heat to a sufficient extent in order to commence at all. This balance is complicated by the reactant concentration not being constant while passing through the catalyst charge, but rather decreasing.

In the exit region of the reaction gas mixture from the fixed catalyst bed, this has the effect of reducing the reaction rate and the associated evolution of heat, while, in the entrance region of the reaction gas mixture into the catalyst charge, the high reactant concentration accelerates the exothermic evolution of heat.

The above-described state of affairs is additionally complicated by a fresh fixed catalyst bed not having steady-state activity behavior, but rather passing through what is known as a conditioning phase.

In order to prevent excessive, in some cases uncontrolled, localized evolution of heat when bringing a fresh catalyst charge on stream, WO 02/098827 recommends changing the composition of the charging gas mixture with time in such a way that a charging gas mixture having a very low content of the organic compound to be partially oxidized (typically from 0 to ≦0.5% by volume) is initially used for at least one hour. Subsequently, the reactant content in the charging gas mixture is increased in stages. At the same time as the reactant concentration in the charging gas mixture increases, the reactant ratio is varied. Finally, a charging gas mixture having a substantially constant composition is conducted over the fixed catalyst bed.

As soon as the charging gas mixture of the organic compound to be partially oxidized comprises, the hourly space velocity of charging gas mixture on the catalyst charge is kept constant.

However, the procedure of WO 02/098827 described is disadvantageous in that, when it is performed over several operating hours, there is no prevailing substantially stable charging gas mixture composition. This is disadvantageous in that the charging gas mixture, depending on its composition, can have explosive and nonexplosive states (cf. DE-A 10232482). Frequent changes in its composition should therefore be avoided.

Furthermore, it is not advantageous to carry out the startup of the gas phase partial oxidation under full load (final hourly space velocity of charging gas mixture on the fixed catalyst bed), since a high hourly space velocity on the fixed catalyst bed causes a short average residence time in the fixed catalyst bed. However, a short residence time curtails the period available for reaction at the catalyst.

It is an object of the present invention to substantially remedy the disadvantages of the procedure of the acknowledged prior art.

We have found that this object is achieved by a process for preparing (meth)acrolein and/or (meth)acrylic acid by heterogeneously catalyzed gas phase partial oxidation by charging a fresh fixed catalyst bed disposed in a reactor at elevated temperature with a charging gas mixture which, in addition to at least one organic precursor compound to be partially oxidized and molecular oxygen as an oxidant, comprises at least one diluent gas which behaves substantially inertly under the conditions of the heterogeneously catalyzed gas phase partial oxidation, which comprises carrying out the process, after the composition of the charging gas mixture has been established, at substantially constant conversion of the organic precursor compound and at substantially constant composition of the charging gas mixture, initially over a startup period of from 3 days to 10 days at a low hourly space velocity and subsequently at a higher hourly space velocity, of the charging gas mixture on the catalyst charge.

In this context, the hourly space velocity of charging gas mixture on a fixed catalyst bed of a reaction stage refers to the amount of charging gas mixture in liters at STP (=1 (STP); the volume in liters which would be taken up under standard conditions, i.e. at 25° C. and 1 bar, by the amount of charging gas mixture in question) which is conducted through one liter of fixed catalyst bed per hour (upstream and downstream beds of pure inert material are not counted as part of the fixed catalyst bed; in contrast, homogeneous mixtures of shaped inert material bodies and shaped catalyst bodies are counted as being part of the fixed catalyst bed).

The advantage of the process according to the invention over the prior art process is based on the fact that it curtails excessive heat evolution not by reducing the reactant content of the charging gas mixture, but rather, at full reactant content, by reducing the hourly space velocity of charging gas mixture on the fixed catalyst bed.

The conversion of the organic precursor compound (based on single pass of the charging gas mixture through the fixed catalyst bed) is set substantially constantly to the desired target conversion. In this context, substantially constantly means that the maximum deviation of the arithmetic average conversion over time is not more than ±10%, preferably not more than ±5% (the basis is the arithmetic average conversion over time).

Equally, in the present context, "at substantially constant composition of the charging gas mixture" means that the maximum deviation of the proportion by volume of one of the components (molecular oxygen, organic precursor compound and inert diluent gas) of the charging gas mixture from the particular arithmetic average proportion by volume over time of the particular component of the charging gas mixture is not more than ±10%, preferably not more than ±5% (the basis is the particular arithmetic average proportion by volume over time of the particular component of the charging gas mixture).

The composition of the charging gas mixture, and also the temperature of the fixed catalyst bed, for the process according to the invention can in principle be established by the procedure described in WO 02/098827. However, the period required for this purpose is normally distinctly below one hour. However, it can also be effected by adding, in a line leading through a static mixer, to the reactor containing the fixed catalyst bed charge, initially only inert gas (including steam) (optionally with a content of from 2 to 4% by volume of oxygen), then the at least one organic precursor compound and finally the oxygen source (normally air). The fixed catalyst bed is brought to the temperature at which the low hourly space velocity is required as early as during the inert gas feed by means of the heat carrier, in order to achieve the target conversion on single pass through the catalyst charge.

A low hourly space velocity of charging gas mixture on the fixed catalyst bed at substantially constant composition of the charging gas mixture is equivalent to a low hourly space velocity of reactant on the fixed catalyst bed.

When the hourly space velocity of charging gas mixture on the fixed catalyst bed is increased in the later course of the process according to the invention, this reduces the average residence time of the reactants in the catalyst charge. In order to achieve a substantially constant conversion at a short residence time of the at least one organic precursor compound, it is therefore normally necessary to increase the temperature of the heat carrier used for the indirect heat exchange.

In the process according to the invention, low hourly space velocity of charging gas mixture on the fixed catalyst bed means that the low hourly space velocity is typically from 40 to 80%, preferably from 50 to 70%, of the higher desired (final) hourly space velocity for which the reactor including its catalyst charge is designed.

In other words, if the reactor and the fixed catalyst bed are designed for a final hourly space velocity of, for example, 150 l (STP) of propene/l of fixed catalyst bed·h (the propene content in the charging gas mixture of a propene partial oxidation to acrolein and/or acrylic acid is typically from 4 to 12% by volume), the inventive 3- to 10-day startup is typically carried out at an hourly space velocity of 100 l (STP) of propene/l·h. However, the aforementioned startup could also be carried out at appropriate hourly space velocities of from 80 to 120 l (STP) of propene/l·h.

If a final hourly space velocity of from 180 to 190 l (STP) of propene/l·h is intended, the inventive 3- to 10-day startup is typically carried out at an hourly space velocity of 120 l (STP) of propene/l·h. However, the aforementioned startup could also be carried out at appropriate hourly space velocities of from 100 to 140 l (STP) of propene/l·h. In general, the desired final hourly space velocity of organic precursor compound is at values of $\geq 80$ l (STP)/l·h, usually at values of $\geq 100$ l (STP)/l·h or of $\geq 120$ l (STP)/l·h. Final hourly space velocities of 600 l (STP)/l·h or in many cases 300 l (STP)/l·h are generally not exceeded.

After the startup period, the hourly space velocity can be increased to the desired final hourly space velocity sharply, continuously or stepwise.

The advantage of the process according to the invention is that on completion of the startup phase of from 3 to 10 days, frequently from 4 to 9 or from 5 to 8 days, it enables the process to be continued at higher hourly space velocity with comparatively increased target product selectivity and at the same time comparatively lower heat carrier temperature. The basis for comparison in this case is a shortened or absent startup phase at lower hourly space velocity. The process also enables minimum hotspot temperatures (the term for the highest temperature within the fixed catalyst bed flowed through by reaction gas mixture).

Useful fixed bed catalysts for the process according to the invention for preparing (meth)acrolein, in particular for preparing acrolein from propene, are all of those whose active composition is at least one multimetal oxide containing Mo, Bi and Fe. They are to be referred to here as fixed bed catalysts 1.

In other words, the fixed bed catalysts 1 used may in principle be any of those disclosed in the documents DE-C 3338380, DE-A 19902562, EP-A 15565, DE-C 2380765, EP-A 807465, EP-A 279374, DE-A 3300044, EP-A 575897, U.S. Pat. No. 4,438,217, DE-A 19855913, WO 98/24746, DE-A 19746210 (those of the general formula II), JP-A 91/294239, EP-A 293224 and EP-A 700714. This is true in particular of the exemplary embodiments in these documents, among which particular preference is given to those of EP-A 15565, EP-A 575897, DE-A 19746210 and DE-A 19855913. In this context, particular emphasis is given to a catalyst according to example 1c of EP-A 15565 and also to a catalyst to be prepared in a corresponding manner but whose active composition, has the composition $Mo_{12}Ni_{6.5}Zn_2Fe_2Bi_1P_{0.0065}K_{0.06}O_x \cdot 10SiO_2$. Emphasis is further given to the example having the serial no. 3 of DE-A 19855913 (stoichiometry: $Mo_{12}Co_7Fe_3Bi_{0.6}K_{0.08}Si_{1.6}O_x$) as an unsupported hollow cylinder catalyst of geometry 5 mm×3 mm×2 mm (external diameter×height×internal diameter) and also to the multimetal oxide II unsupported catalyst according to example 1 of DE-A 19746210. The multimetal oxide catalysts of U.S. Pat. No. 4,438,217 should also be mentioned. The latter is particularly true when these hollow cylinders have a geometry of 5 mm×2 mm×2 mm, or 5 mm×3 mm×2 mm, or 6 mm×3 mm×3 mm, or 7 mm×3 mm×4 mm (each external diameter×height×internal diameter).

A multitude of the multimetal oxide active compositions suitable for fixed bed catalysts 1 can be encompassed the general formula I

  (I)

where the variables are defined as follows:
$X^1$=nickel and/or cobalt,
$X^2$=thallium, an alkali metal and/or an alkaline earth metal,
$X^3$=zinc, phosphorus, arsenic, boron, antimony, tin, cerium, lead and/or tungsten,
$X^4$=silicon, aluminum, titanium and/or zirconium,
a=0.5 to 5,
b=0.01 to 5, preferably 2 to 4,
c=0 to 10, preferably 3 to 10,
d=0 to 2, preferably 0.02 to 2,
e=0 to 8, preferably 0 to 5,
f=0 to 10 and
n=a number which is determined by the valency and frequency of the elements other than oxygen in 1.

They are obtainable in a manner known per se (see, for example, DE-A 4023239) and are customarily shaped in bulk to give spheres, rings or cylinders or used in the form of coated catalysts, i.e. preshaped inert support bodies coated with the active composition. However, it will be appreciated that they may also be used in powder form as fixed bed catalyst 1. It will be appreciated that the fixed bed catalyst 1 used may also be the multimetal oxide catalyst ACS-4 from Nippon Shokubai comprising Bi, Mo and Fe in accordance with the invention.

In principle, active compositions suitable for fixed bed catalysts 1, in particular those of the general formula I, can be prepared in a simple manner by generating a very intimate, preferably finely divided dry mixture having a composition corresponding to its stoichiometry from suitable sources of its elemental constituents and calcining it at temperatures of from 350 to 650° C. The calcination may be effected either under inert gas or under an oxidative atmosphere, for example air (mixture of inert gas and oxygen), or under a reducing atmosphere (for example a mixture of inert gas, $NH_3$, CO and/or $H_2$). The calcination time may be from a few minutes to a few hours and customarily falls with temperature. Useful sources of the elemental constituents of the multimetal oxide active compositions I include those compounds which are already oxides and/or those compounds which can be converted to oxides by heating, at least in the presence of oxygen.

In addition to the oxides, other useful starting compounds are in particular halides, nitrates, formates, oxalates, citrates, acetates, carbonates, amine complexes, ammonium salts and/or hydroxides (compounds such as $NH_4OH$, $(NH_4)_2CO_3$, $NH_4NO_3$, $NH_4CHO_2$, $CH_3COOH$, $NH_4CH_3CO_2$ and/ or ammonium oxalate which decompose and/or fall apart on subsequent calcining at the latest to give compounds released in gaseous form may additionally be incorporated in the intimate dry mixture).

The intimate mixing of the starting compounds for preparing multimetal oxide active compositions I may be effected in dry or wet form. Where it is effected in dry form, the starting compounds are advantageously used as fine powders and subjected to calcination after mixing and optionally compacting. However, preference is given to effecting the intimate mixing in wet form. Customarily, the starting compounds are mixed with each other in the form of an aqueous solution and/or suspension. Particularly intimate dry mixtures are obtained in the mixing process described when the starting materials are exclusively sources of the elemental constituents present in dissolved form. The solvent used is preferably water. The aqueous composition obtained is then dried, and the drying procedure is preferably effected by spray drying the aqueous mixture at exit temperatures of from 100 to 150° C.

The multimetal oxide compositions suitable in accordance with the invention as fixed bed catalysts 1, in particular those of the general formula I, may be used for the process according to the invention either in powder form or shaped into certain catalyst geometries, in which case the shaping may be effected before or after the final calcination. For example, unsupported catalysts may be prepared from the powder form of the active composition or its uncalcined and/or partially calcined precursor composition by compacting to the desired catalyst geometry (for example by tableting, extruding or pressing to give strands), in the course of which assistants, for example graphite or stearic acid as lubricants and/or shaping assistants and reinforcing agents such as microfibers of glass, asbestos, silicon carbide or potassium titanate, may optionally be added. Examples of useful unsupported catalyst geometries include solid cylinders or hollow cylinders having an external diameter and a length of from 2 to 10 mm. In the case of the hollow cylinders, a wall thickness of from 1 to 3 mm is appropriate. It will be appreciated that the unsupported catalyst may also have spherical geometry, in which case the sphere diameter may be from 2 to 10 mm.

It will be appreciated that the pulverulent active composition or its pulverulent precursor composition which has as yet only been partially calcined, if at all, may also be shaped by applying to preshaped inert catalyst supports. The coating of the support bodies for preparing the coated catalysts is generally performed in a suitable rotatable vessel, as disclosed, for example, in DE-A 2909671, EP-A 293859 or EP-A 714700. To coat the support bodies, the pulverulent composition to be applied is appropriately moistened and dried again after application, for example by means of hot air. The layer thickness of the pulverulent composition applied to the support bodies is appropriately selected within the range from 10 to 1000 mm, preferably within the range from 50 to 500 mm and more preferably within the range from 150 to 250 mm.

Useful support materials may be customary porous or nonporous aluminum oxides, silicon dioxide, thorium dioxide, zirconium dioxide, silicon carbide or silicates such as magnesium or aluminum silicate. The support bodies may have a regular or irregular shape, although preference is given to regularly shaped support bodies having distinct surface roughness, for example spheres or hollow cylinders. The use of substantially nonporous, spherical supports having surface roughness and made of steatite whose diameter is from 1 to 8 mm, preferably from 4 to 5 mm, is suitable. However, useful support bodies are also cylinders whose length is from 2 to 10 mm and whose external diameter is from 4 to 10 mm. In the case of rings suitable as support bodies according to the invention, the wall thickness is further customarily from 1 to 4 mm. Annular support bodies to be used with preference according to the invention have a length of from 3 to 6 mm, an external diameter of from 4 to 8 mm and a wall thickness of from 1 to 2 mm. In particular, rings of geometry 7 mm×3 mm×4 mm (external diameter×length×internal diameter) are also suitable as support bodies according to the invention. It will be appreciated that the fineness of the catalytically active oxide compositions to be applied to the surface of the support body is adapted to the desired coating thickness (cf. EP-A 714 700).

Multimetal oxide active compositions to be used according to the invention which are appropriate as fixed bed catalysts 1 are also compositions of the general formula II

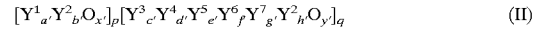  (II)

where the variables are defined as follows:
$Y^1$=bismuth, tellurium, antimony, tin and/or copper,
$Y^2$=molybdenum and/or tungsten,
$Y^3$=an alkali metal, thallium and/or samarium,
$Y^4$=an alkaline earth metal, nickel, cobalt, copper, manganese, zinc, tin, cadmium and/or mercury,
$Y^5$=iron, chromium, cerium and/or vanadium,
$Y^6$=phosphorus, arsenic, boron and/or antimony,
$Y^7$=a rare earth metal, titanium, zirconium, niobium, tantalum, rhenium, ruthenium, rhodium, silver, gold, aluminum, gallium, indium, silicon, germanium, lead, thorium and/or uranium,
a'=0.01 to 8,
b'=0.1 to 30,
c'=0 to 4,
d'=0 to 20,
e'=0 to20,
f'=0 to 6,
g'=0 to 15,
h'=8 to 16,
x', y'=numbers which are determined by the valency and frequency of the elements other than oxygen in II and
p, q=numbers whose p/q ratio is from 0.1 to 10, containing three-dimensional regions of the chemical composition $Y^1_{a'}Y^2_{b'}O_{x'}$ which are delimited from their local environment owing to their different composition to the local environment and whose largest diameter (longest line passing through the center of the region and connecting two points on the surface (interface) of the region) is from 1 nm to 100 μm, frequently from 10 nm to 500 nm or from 1 μm to 50 or 25 μm.

Particularly advantageous multimetal oxide compositions II according to the invention are those in which $Y^1$ is bismuth.

Among these, preference is given in turn to those which correspond to the general formula III

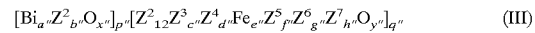  (III)

where the variables are defined as follows:
$Z^2$=molybdenum and/or tungsten,
$Z^3$=nickel and/or cobalt, $Z^4$=thallium, an alkali metal and/or an alkaline earth metal,
$Z^5$=phosphorus, arsenic, boron, antimony, tin, cerium and/or lead,
$Z^6$=silicon, aluminum, titanium and/or zirconium,
$Z^7$=copper, silver and/or gold,
a"=0.1 to 1,
b"=0.2 to 2,
c"=3 to 10,
d"=0.02 to 2,
e"=0.01 to 5, preferably 0.1 to 3,
f"=0 to 5,
g"=0 to 10,
h"=0 to 1,
x", y"=numbers which are determined by the valency and frequency of the elements other than oxygen in III,
p", q"=numbers whose p"/q" ratio is from 0.1 to 5, preferably from 0.5 to 2, and very particular preference is given to those compositions III where $Z^2{}_{b''}$=(tungsten)$_{b''}$ and $Z^2{}_{12}$=(molybdenum)$_{12}$.

It is further advantageous when at least 25 mol % (preferably at least 50 mol % and more preferably at least 100 mol %) of the entire $[Y^1{}_a Y^2{}_b O_{x'}]_p([Bi_{a''} Z^2{}_{b''} O_{x''}]_{p''})$ proportion of the multimetal oxide compositions II (multimetal oxide compositions II) suitable according to the invention as fixed bed catalysts 1 in the multimetal oxide compositions II (multimetal oxide compositions II) suitable according to the invention is in the form of three-dimensional regions of the chemical composition $Y^1{}_a Y^2{}_b O_{x'}[Bi_{a''} Z^2{}_{b''} O_{x''}]$ which are delimited from their local environment owing to their different chemical composition from their local environment and whose largest diameter is in the range from 1 nm to 100 μm.

With regard to the shaping, the same applies to multimetal oxide composition 11 catalysts as was said for multimetal oxide composition I catalysts.

The preparation of multimetal oxide composition II active compositions is described, for example, in EP-A 575897 and also in DE-A 19855913.

It is appropriate from an application point of view to carry out the heterogeneously catalyzed gas phase partial oxidation of an organic precursor compound to (meth)acrolein in a tube bundle reactor charged with the fixed bed catalysts 1 as described, for example, in EP-A 700714.

In other words, in the simplest manner, the fixed bed catalyst 1 to be used is disposed in the metal tubes of a tube bundle reactor and a heating medium (one-zone method), generally a salt melt, is conducted around the metal tubes. Salt melt and reaction gas mixture can be conducted in a simple cocurrent or countercurrent flow. However, the salt melt (the heating medium) can also be conducted, viewed over the reactor, in a meandering manner around the tube bundles, in such a way that only viewed over the entire reactor does a cocurrent or countercurrent to the flow direction of the reaction gas mixture exist. The flow rate of the heating medium (heat exchange medium) is typically such that the temperature rise (caused by the exothermicity of the reaction) of the heat exchange medium from the entry point into the reactor to the exit point out of the reactor is from $\geq 0$ to 10° C., frequently from $\geq 2$ to 8° C., often from $\geq 3$ to 6° C. The entrance temperature of the heat exchange medium into the tube bundle reactor, especially in the case of the conversion of propene to acrolein, is generally from 310 to 360° C., frequently from 320 to 340° C.

Suitable heat exchange media are in particular fluid heating media. It is particularly favorable to use melts of salts such as potassium nitrate, potassium nitrite, sodium nitrite and/or sodium nitrate, or of low-melting metals such as sodium, mercury and also alloys of different metals.

It is appropriate to feed the charging gas mixture to the charge of fixed bed catalyst 1 preheated to the desired reaction temperature.

Especially in the case of the desired high (for example $\geq 160$ 1 (STP)/l·h, but generally $\leq 600$ 1 (STP)/l·h) final hourly space velocities of the at least one organic precursor compound to be partially oxidized (for example of propene) on the charge of fixed bed catalyst 1, it is appropriate to carry out the process according to the invention in a two-zone tube bundle reactor. A preferred variant of a two-zone tube bundle reactor which can be used in accordance with the invention is disclosed by DE-C 2830765. However, the two-zone tube bundle reactors disclosed in DE-C 2513405, U.S. Pat. No. 3,147,084, DE-A 2201528, EP-A 383224 and DE-A 2903218 are also suitable.

In other words, in the simplest manner, the fixed bed catalyst 1 to be used is disposed in the metal tubes of a tube bundle reactor and two substantially spatially separated heating media, generally salt melts, are conducted around the metal tubes. The tube section over which the particular salt bath extends represents a reaction zone. Preferably, for example, a salt bath A flows around that section of the tubes (the reaction zone A) in which, for example, the oxidative conversion of propene (on single pass) proceeds until a conversion in the range from 40 to 80 mol % is achieved, and a salt bath B flows around, for example, the section of the tubes (the reaction zone B) in which, for example, the subsequent oxidative conversion of propene (on single pass) proceeds until a conversion value of generally at least 90 mol % is achieved (if required, further reaction zones which are kept at individual temperatures may follow the reaction zones A, B).

Within the particular temperature zone, the salt bath can in principle be conducted as in the one-zone method. The temperature of the salt bath B is normally at least 5° C. above the temperature of the salt bath A.

Otherwise, the two-zone high load method can be carried out, for example, as described in DE-A 19948523 or as described in DE-A 19948248.

The example of the gas phase partial oxidation of propene to acrolein will now be used by way of example to provide more details. The other gas phase partial oxidations according to the invention of organic precursor compounds can be carried out in a similar manner.

Accordingly, the process according to the invention is suitable for propene hourly space velocities on the fixed bed catalyst charge 1 of $\geq 70$ 1 (STP)/l·h, $\geq 130$ 1 (STP)/l·h, $\geq 180$ 1 (STP)/l·h, $\geq 240$ 1 (STP)/l·h, $\geq 300$ 1 (STP)/l·h, but normally $\leq 600$ 1 (STP)/l·h.

The inert gas to be used for the charging gas mixture may consist of $\geq 20\%$ by volume, or $\geq 30\%$ by volume, or $\geq 40\%$ by volume, or $\geq 50\%$ by volume, or $\geq 60\%$ by volume, or $\geq 70\%$ by volume, or $\geq 80\%$ by volume, or $\geq 90\%$ by volume, or $\geq 95\%$ by volume, of molecular nitrogen.

However, at propene hourly space velocities on the fixed bed catalyst charge 1 of above 250 1 (STP)/l·h, the use is recommended for the process according to the invention of inert (inert diluent gases here are intended generally to refer to those of which less than 5%, preferably less than 2%, is converted on single pass through the particular fixed bed catalyst charge) diluent gases such as propane, ethane, methane, pentane, butane, $CO_2$, CO, steam and/or noble gases for the charging gas mixture.

With increasing propene hourly space velocity, the two-zone method described, as already mentioned, is preferred over the one-zone method described.

The working pressure in the process according to the invention in the propene partial oxidation may be either below atmospheric pressure (for example down to 0.5 bar) or above atmospheric pressure. Typically, the working pressure will be at values of from 1 to 5 bar, frequently from 1.5 to 3.5 bar. Normally, the reaction pressure in the propene partial oxidation will not exceed 100 bar.

The molar $O_2:C_3H_6$ ratio in the charging gas mixture is normally $\geq 1$. Typically, this ratio will be at values $\leq 3$. Frequently, the molar $O_2:C_3H_6$ ratio in the charging gas mixture will be $\geq 1.5$ and $\leq 2.0$.

Useful sources for the molecular oxygen required are either air or, for example, air depleted in molecular nitrogen (for example $\geq 90\%$ by volume of $O_2$, 10% by volume of $N_2$).

The propene fraction in the charging gas mixture may be, for example, at values of from 4 to 15% by volume, frequently from 5 to 12% by volume or from 5 to 8% by volume (based in each case on the total volume).

Frequently, the process according to the invention will be carried out at a propene:oxygen:inert gases (including steam) volume ratio in the starting reaction gas mixture (charging gas mixture) of 1:(1.0 to 3.0):(5 to 25), preferably 1:(1.5 to 2.3):(10 to 15). However, the charging gas mixture compositions of DE-A 10313209 can also be employed in accordance with the invention.

To prepare acrylic acid from acrolein, useful [lacuna] for the process according to the invention are all those whose active composition is at least one multimetal oxide containing Mo and V. They are to be referred to here as fixed bed catalysts 2.

Such suitable fixed bed catalysts 2 can be taken, for example, from U.S. Pat. No. 3,775,474, U.S. Pat. No. 3,954,855, U.S. Pat. No. 3,893,951 and U.S. Pat. No. 4,339,355. Also particularly suitable are the multimetal oxide compositions of EP-A 427 508, DE-A 2 909 671, DE-C 31 51 805, DE-AS 2 626 887, DE-A 43 02 991, EP-A 700 893, EP-A 714 700 and DE-A 19 73 6105 for fixed bed catalysts 2. Particular preference is given in this context to the exemplary embodiments of EP-A 714 700, and also of DE-A 19 73 6105.

A multitude of the multimetal oxide active compositions suitable as fixed bed catalysts 2 can be encompassed by the general formula IV

$$Mo_{12}V_aX^1_bX^2_cX^3_dX^4_eX^5_fX^6_gO_n \quad (IV)$$

in which the variables are defined as follows:
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals,
$X^5$=one or more alkaline earth metals,
$X^6$=Si, Al, Ti and/or Zr,
a=1 to 6,
b=0.2 to 4,
c=0.5 to 18,
d=0 to 40,
e=0 to 2,
f=0 to 4,
g=0 to 40 and
n=a number which is determined by the valency and frequency of the elements other than oxygen in IV.

Preferred embodiments among the active multimetal oxides IV are those which are encompassed by the following definitions of the variables of the general formula IV:
$X^1$=W, Nb, and/or Cr,
$X^2$=Cu, Ni, Co, and/or Fe,
$X^3$=Sb,
$X^4$=Na and/or K,
$X^5$=Ca, Sr and/or Ba,
$X^6$=Is, Al, and/or Ti,
a=1.5 to 5,
b=0.5 to 2,
c=0.5 to 3,
d=0 to 2,
e=0 to 0.2,
f=0 to 1 and
n=a number which is determined by the valency and frequency of the elements other than oxygen in IV.

However, very particularly preferred multimetal oxides IV are those of the general formula V

$$Mo_{12}V_{a'}Y^1_{b'}Y^2_{c'}Y^5_{f'}Y^6_{g'}O_n \quad (V)$$

where
$Y^1$=W and/or Nb,
$Y^2$=Cu and/or Ni,
$Y^5$=Ca and/or Sr,
$Y^6$=Is and/or Al,
a'=2 to 4,
b'=1 to 1.5,
c'=1 to 3,
f=0 to 0.5
g'=0 to 8 and
n'=a number which is determined by the valency and frequency of the elements other than oxygen in V.

The multimetal oxide active compositions (IV) suitable according to the invention are obtainable in a manner known per se, for example as disclosed in DE-A 4335973 or in EP-A 714700.

In principle, multimetal oxide active compositions suitable according to the invention for fixed bed catalysts 2, in particular those of the general formula IV, can be prepared in a simple manner by generating a very intimate, preferably finely divided dry mixture having a composition corresponding to its stoichiometry from suitable sources of its elemental constituents and calcining it at temperatures of from 350 to 600° C. The calcination may be effected either under inert gas or under an oxidative atmosphere, for example air (mixture of inert gas and oxygen), or else under a reducing atmosphere (for example mixtures of inert gas and reducing gases such as $H_2$, $NH_3$, CO, methane and/or acrolein, or the reducing gases alone). The calcination time may be from a few minutes to a few hours and customarily falls with temperature. Useful sources of the elemental constituents of the multimetal oxide active compositions IV include those compounds which are already oxides and/or those compounds which can be converted to oxides by heating, at least in the presence of oxygen.

The intimate mixing of the starting compounds for preparing multimetal oxide active compositions IV may be effected in dry or wet form. Where it is effected in dry form, the starting compounds are appropriately used as fine powders and subjected to calcination after mixing and optionally compacting. However, preference is given to effecting the intimate mixing in wet form.

Customarily, the starting compounds are mixed with each other in the form of an aqueous solution and/or suspension. Particularly intimate dry mixtures are obtained in the mixing process described when the starting materials are exclusively sources of the elemental constituents present in dissolved form. The solvent used is preferably water. The aqueous composition obtained is then dried, and the drying procedure is preferably effected by spray drying the aqueous mixture at exit temperatures of from 100 to 150° C.

The multimetal oxide compositions suitable in accordance with the invention as fixed bed catalysts 2, in particular those of the general formula IV, may be used for the process according to the invention either in powder form or shaped into certain catalyst geometries, in which case the shaping may be effected before or after the final calcination. For example, unsupported catalysts may be prepared from the powder form of the active composition or its uncalcined precursor composition by compacting to the desired catalyst geometry (for example by tableting, extruding or pressing to give strands), in the course of which assistants, for example graphite or stearic acid as lubricants and/or shaping assistants and reinforcing agents such as microfibers of glass, asbestos, silicon carbide or potassium titanate, may optionally be added. Examples of useful unsupported catalyst geometries include solid cylinders or hollow cylinders having an external diameter and a length of from 2 to 10 mm. In the case of the hollow cylinders, a wall thickness of from 1 to 3 mm is appropriate. It will be appreciated that the unsupported catalyst may also have spherical geometry, in which case the sphere diameter may be from 2 to 10 mm.

It will be appreciated that the pulverulent active composition or its pulverulent precursor composition which has not yet been calcined may also be shaped by applying to preshaped inert catalyst supports. The coating of the support bodies for preparing the coated catalysts is generally performed in a suitable rotatable vessel, as disclosed, for example, in DE-A 2909671, EP-A 293859 or EP-A 714700.

To coat the support bodies, the pulverulent composition to be applied is appropriately moistened and dried again after application, for example by means of hot air. The layer thickness of the pulverulent composition applied to the support bodies is appropriately selected within the range from 10 to 1000 μm, preferably within the range from 50 to 500 μm and more preferably within the range from 150 to 250 μm.

Useful support materials may be customary porous or nonporous aluminum oxides, silicon dioxide, thorium dioxide, zirconium dioxide, silicon carbide or silicates such as magnesium or aluminum silicate. The support bodies may have a regular or irregular shape, although preference is given to regularly shaped support bodies having distinct surface roughness, for example spheres or hollow cylinders. The use of substantially nonporous, spherical supports having surface roughness and made of steatite whose diameter is from 1 to 8 mm, preferably from 4 to 5 mm, is suitable. However, useful support bodies are also cylinders whose length is from 2 to 10 mm and whose external diameter is from 4 to 10 mm. In the case of rings suitable as support bodies according to the invention, the wall thickness is further customarily from 1 to 4 mm. Annular support bodies to be used with preference according to the invention have a length of from 3 to 6 mm, an external diameter of from 4 to 8 mm and a wall thickness of from 1 to 2 mm. In particular, rings of geometry 7 mm×3 mm×4 mm (external diameter×length×internal diameter) are also suitable as support bodies according to the invention. It will be appreciated that the fineness of the catalytically active oxide compositions to be applied to the surface of the support body is adapted to the desired coating thickness (cf. EP-A 714 700).

Favorable multimetal oxide active compositions to be used in accordance with the invention as fixed bed catalysts 2 are also compositions of the general formula VI, $$[D]_p[E]_q \tag{VI}$$

in which the variables are defined as follows:
$D = Mo_{12}V_{a''}Z^1_{b''}Z^2_{c''}Z^3_{d''}Z^4_{e''}Z^5_{f''}Z^6_{g''}O_{x''}$,
$E = Z^7_{12}Cu_{h''}H_{i''}O_{y''}$,
$Z^1$ = W, Nb, Ta, Cr and/or Ce,
$Z^2$ = Cu, Ni, Co, Fe, Mn and/or Zn,
$Z^3$ = Sb and/or Bi,
$Z^4$ = Li, Na, K, Rb, Cs and/or H
$Z^5$ = Mg, Ca, Sr and/or Ba,
$Z^6$ = Si, Al, Ti and/or Zr,
$Z^7$ = Mo, W, V, Nb and/or Ta,
a'' = 1 to 8,
b'' = 0.2 to 5,
c'' = 0 to 23,
d'' = 0 to 50,
e'' = 0 to 2,
f'' = 0 to 5,
g'' = 0 to 50,
h'' = 4 to 30,
i'' = 0 to 20 and
x'', y'' = numbers which are determined by the valency and frequency of the elements other than oxygen in VI and
p, q = numbers other than zero whose p/q ratio is from 160:1 to 1:1, and which are obtainable by separately preforming a multimetal oxide composition E $$Z^7_{12}Cu_{h''}H_{i''}O_{y''} \tag{E}$$

in finely divided form (starting composition 1) and subsequently incorporating the preformed solid starting composition 1 into an aqueous solution, an aqueous suspension or into a finely divided dry mixture of sources of the elements Mo, V, $Z^1$, $Z^2$, $Z^3$, $Z^4$, $Z^5$, $Z^6$, which contains the aforementioned elements in the stoichiometry D $$Mo_{12}V_{a''}Z^1_{b''}Z^2_{c''}Z^3_{d''}Z^4_{e''}Z^5_{f''}Z^6_{g''} \tag{D}$$

(starting composition 2) in the desired p:q ratio, drying, where appropriate, the resulting aqueous mixture, and calcining the resulting dry precursor composition, before or after its drying to the desired catalyst geometry, at temperatures of from 250 to 600° C.

Preference is given to the multimetal oxide compositions VI in which the preformed solid starting composition 1 is incorporated into an aqueous starting composition 2 at a temperature of <70° C. A detailed description of the preparation of multimetal oxide composition VI catalysts is contained, for example, in EP-A 668104, DE-A 19736105 and DE-A 19528646.

With regard to the shaping, the same applies to multimetal oxide composition VI catalysts as was said for the multimetal oxide composition IV catalysts.

Appropriately from an application point of view, the inventive heterogeneously catalyzed gas phase partial oxidation of acrolein to acrylic acid will be carried out in a tube bundle reactor charged with the fixed bed catalysts 2, as described, for example, in EP-A 700893.

In other words, in the simplest manner, the fixed bed catalyst 2 to be used is disposed in the metal tubes of a tube bundle reactor and a heating medium (one-zone method), generally a salt melt, is conducted around the metal tubes. Salt melt and reaction gas mixture can be conducted in simple cocurrent or countercurrent. However, the heating medium (the salt melt) can also be conducted, viewed over the reactor, in a meandering manner around the tube bundles, in such a way that only when viewed over the entire reactor does a cocurrent or countercurrent to the flow direction of the reaction gas mixture exist. The flow rate of the heating medium (heat exchange medium) is typically such that the temperature rise (caused by the exothermicity of the reaction) of the heat exchange medium from the entry point into the reactor to the exit point from the reactor is from 0 to 10° C., frequently from 2 to 8° C., often from 3 to 6° C. The entry temperature of the heat exchange medium into the tube bundle reactor is generally from 230 to 300° C., frequently from 245 to 285° C. or from 245 to 265° C. Suitable heat exchange media are the same fluid heating media as already described for the inventive heterogeneously catalyzed gas phase partial oxidation of an organic precursor compound to (meth)acrolein.

The charging gas mixture is appropriately fed to the charge of fixed bed catalyst 2 preheated to the desired reaction temperature.

Especially in the case of desired high (for example $\geq 140$ l (STP)/l·h, but generally $\leq 600$ l (STP)/l·h) final hourly space velocities of acrolein on the charge of fixed bed catalyst 2, it is appropriate to carry out the process, according to the invention in a two-zone tube bundle reactor. A preferred variant of a two-zone tube bundle reactor which can be used in accordance with the invention for this purpose is disclosed by DE-C 2830765. However, the two-zone tube bundle reactors disclosed in DE-C 2513405, U.S. Pat. No. 3,147,084, DE-A 2201528, EP-A 383224 and DE-A 2903582 are also suitable.

In other words, in a simple manner, the fixed bed catalyst 2 to be used in accordance with the invention is disposed in the metal tubes of a tube bundle reactor, and two substantially spatially separated heating media, generally salt melts, are conducted around the metal tubes. The tube section over which the particular salt bath extends represents a reaction zone.

Preferably, for example, a salt bath C flows around those sections of the tubes (the reaction zone C) in which the oxidative conversion of acrolein (on single pass) proceeds until a conversion value in the range from 55 to 85 mol % is achieved, and a salt bath D flows around the section of the tubes (the reaction zone D) in which the subsequent oxidative conversion of acrolein (on single pass) proceeds until a conversion value of generally at least 90 mol % is achieved (if required, further reaction zones which are kept at individual temperatures may follow the reaction zones C,D to be employed in accordance with the invention).

Within the particular temperature zone, the salt bath can in principle be conducted as in the one-zone method. The temperature of the salt bath D is normally at least 5 to 10° C. above the temperature of the salt bath C.

Otherwise, the two-zone high-load method can be carried out as described, for example, in DE-A 19948523 or as described in DE-A 19948248.

Accordingly, the process according to the invention is suitable for acrolein hourly space velocities on the fixed bed catalyst charge 2 of $\geq 70$ l (STP)/l·h, $\geq 130$ l (STP)/l·h, $\geq 180$ l (STP)/l·h, $\geq 240$ l (STP)/l·h, $\geq 300$ l (STP)/l·h, but normally $\leq 600$ l (STP)/l·h.

The inert gas to be used for the charging gas mixture may consist of $\geq 20\%$ by volume, or $\geq 30\%$ by volume, or $\geq 40\%$ by volume, or $\geq 50\%$ by volume, or $\geq 60\%$ by volume, or $\geq 70\%$ by volume, or $\geq 80\%$ by volume, or $\geq 90\%$ by volume, or $\geq 95\%$ by volume, of molecular nitrogen.

If the gas phase partial oxidation of acrolein is the second reaction stage of a two-stage gas phase partial oxidation of propene to acrylic acid, the inert diluent gas will frequently consist of from 5 to 20% by weight of $H_2O$ (is formed in the first reaction stage) and of from 70 to 90% by volume of $N_2$.

However, at acrolein hourly space velocities on the fixed bed catalyst 2 of above 250 l (STP)/l·h, it is recommended for the process according to the invention to use inert diluent gases such as propane, ethane, methane, butane, pentane, $CO_2$, CO, steam and/or noble gases. It will be appreciated that these gases can also be used even at relatively low acrolein hourly space velocities.

The working pressure in the gas phase partial oxidation of acrolein may be either below atmospheric pressure (for example up to 0.5 bar) or above atmospheric pressure. Typically, the working pressure in the gas phase partial oxidation of acrolein will be at values of from 1 to 5 bar, frequently from 1 to 3 bar.

Normally, the reaction pressure in the acrolein partial oxidation will not exceed 100 bar.

The molar $O_2$:acrolein ratio in the charging gas mixture of the fixed bed catalyst charge 2 tube will normally be $\geq 1$. Typically, this ratio will be at values of $\leq 3$. According to the invention, the molar $O_2$:acrolein ratio in the aforementioned charging gas mixture will be from 1 to 2 or from 1 to 1.5. In many cases, the process according to the invention in the case of acrolein partial oxidation will be performed at an acrolein:oxygen:steam:inert gas volume ratio (l (STP)) in the charging gas mixture of 1:(1 to 3):(0 to 20):(3 to 30), preferably of 1:(1 to 3):(0.5 to 10).

The acrolein fraction in the charging gas mixture may be, for example, at values of from 3 to 15% by volume, frequently from 4 to 10% by volume or from 5 to 8% by volume (based in each case on the total volume).

The heterogeneously catalyzed gas phase partial oxidation of methacrolein to methacrylic acid can be carried out in a similar manner to that of acrolein to acrylic acid. However, the catalysts used are preferably those of EP-A 668103. The remaining reaction conditions are likewise advantageously established in accordance with EP-A 668103.

For the gas phase partial oxidation of propane to acrylic acid or of isobutane to methacrylic acid, the multimetal oxide catalysts used will advantageously be those recommended, for example, by the documents DE-A 10248584, DE-A 10029338, DE-A 10033121, DE-A 10261186, DE-A 10254278, DE-A 10034825, EP-A 962253, EP-A 1260495, DE-A 10122027, EP-A 1192987 and DE-A 10254279.

The reaction conditions can likewise be selected in accordance with these documents.

The reactor used will typically be a one-zone reactor.

Finally, it is emphasized that, in a two-stage heterogeneously catalyzed gas phase partial oxidation for preparing (meth)acrylic acid (for example from propene to acrolein ($1^{st}$ stage) and then acrolein to acrylic acid ($2^{nd}$ stage)), in which the product gas mixture of the first stage, optionally after cooling and metering in of air as an oxygen source, is conducted into the second stage, application of the process according to the invention to the first stage is automatically accompanied by application of the process according to the invention to the second stage.

It is also emphasized that, in the process according to the invention, at the transition from the low hourly space velocity to the higher hourly space velocity, it may be appropriate to slightly reduce the cycle gas fraction in the charging gas mixture (the reactant fraction in the charging gas mixture then rises slightly). The aforementioned is appropriate when the design of the cycle gas compressor limits the maximum compressible amount of gas. Finally it is emphasized that the process according to the invention can also be employed on freshly regenerated (for example according to EP-A 169449, EP-A 614872, EP-A 339119, DE-A 10249797 or DE-A 10350822) catalyst beds disposed in reactors.

EXAMPLE AND COMPARATIVE EXAMPLES a) Experimental Arrangement

A reaction tube (V2A steel; external diameter 30 mm, wall thickness 2 mm, internal diameter 26 mm, length: 350 cm and a thermal tube (external diameter 4 mm), centered in the middle of the reaction tube, to accommodate a thermoelement which can be used to determine the temperature in the reaction tube over its entire length) was freshly charged from top to bottom as follows:

Section 1: length 80 cm
  Steatite rings of geometry 7 mm×7 mm×4 mm (external diameter×length×internal diameter) as a preliminary bed.
Section 2: length 100 cm
  Catalyst charge of a homogeneous mixture of 30% by weight of steatite rings of geometry 5 mm×3 mm×2 mm (external diameter×length×internal diameter) and 70% by weight of unsupported catalyst from section 3.
Section 3: length 170 cm
  Catalyst charge of annular (5 mm×3 mm×2 mm=external diameter×length×internal diameter) unsupported catalyst according to Example 1 of DE-A 10046957 (stoichiometry: $[Bi_2W_2O_9 \cdot 2WO_3]_{0.5}[Mo_{12}Co_{5.5}Fe_{2.94}Si_{1.59}K_{0.08}O_x]_1)$.
The reaction tube is heated by means of a salt bath pumped in countercurrent.

b) Experimental Procedure

The experimental arrangement described, in each case freshly prepared, was in each case charged continuously with a charging gas mixture (mixture of air, polymer-grade propylene and cycle gas) of the composition 5.4% by volume of propene, 10.5% by volume of oxygen, 1.2% by volume of $CO_x$, 81.3% by volume of $N_2$, and 1.6% by volume of $H_2O$, and the hourly space velocity and the thermostatting of the reaction tube were varied over time. The reaction tube was thermostatted in such a way that the propene conversion C (mol %) on single pass of the charging gas mixture through the reaction tube continuously was about 95.0 mol %.

The tables which follow show the product of value selectivities $S^P$ (mol %) (sum of the selectivity of acrolein formation and the selectivity of acrylic acid formation) achieved and also the maximum temperatures $T_{max}$ measured along the reaction tube in °C., as a function of the hourly space velocity on the fixed catalyst bed (expressed as propene loading in l (STP)/l·h) and the salt bath temperature $T_S$ (°C.). The desired final hourly space velocity was 150 l (STP)/l·h. The results reported always relate to the end of the particular operating period.

Example

| Operating period | Propene loading (l (STP)/l · h) | C (mol %) | $S^P$ (mol %) | $T_S$ (° C.) | $T_{max}$ (° C.) |
|---|---|---|---|---|---|
| Day 1 to Day 2 | 100 | 95.1 | 93.8 | 328 | 372 |
| Day 3 to Day 9 | 100 | 95.1 | 95.4 | 324 | 368 |
| Day 10 to Day 15 | 130 | 94.9 | 95.6 | 333 | 385 |
| Day 16 to Day 22 | 150 | 95.0 | 95.4 | 339 | 388 |

Comparative Example

| Operating period | Propene loading (l (STP)/l · h) | C (mol %) | $S^P$ (mol %) | $T_S$ (° C.) | $T_{max}$ (° C.) |
|---|---|---|---|---|---|
| Day 1 to Day 3 | 150 | 95.1 | 95.1 | 346 | 401 |
| Day 4 to Day 5 | 150 | 95.0 | 95.2 | 346 | 398 |
| Day 6 to Day 7 | 150 | 94.7 | 95.4 | 349 | 400 |

A comparison of example and comparative example shows that when the fresh catalyst charge is immediately brought on stream under the desired final hourly space velocity, this results in a catalyst charge which requires significantly higher salt bath temperatures for the same conversion. The higher maximum temperatures additionally cause premature aging of the catalyst charge.

U.S. Provisional Patent Application No. 60/49814, filed on Aug. 14, 2003, is incorporated into the present application by literature reference.

With regard to the abovementioned teachings, numerous alterations and deviations from the present invention are possible. It is therefore possible to assume that the invention, within the scope of the appended claims, can be performed in a different way from that specifically decribed herein.

We claim:

1. A process for preparing (meth)acrolein and/or (meth)acrylic acid by heterogeneously catalyzed gas phase partial oxidation by charging a fresh fixed catalyst bed disposed in a reactor at elevated temperature with a charging gas mixture which, in addition to at least one organic precursor compound to be partially oxidized and molecular oxygen as an oxidant, comprises at least one diluent gas which behaves substantially inertly under the conditions of the heterogeneously catalyzed gas phase partial oxidation, which comprises carrying out the process, after the composition of the charging gas mixture has been established, at substantially constant conversion of the organic precursor compound and at substantially constant composition of the charging gas mixture, initially over a startup period of from 3 days to 10 days at a low hourly space velocity and subsequently at a higher hourly space velocity of the charging gas mixture on the catalyst charge.

2. A process as claimed in claim 1, wherein the low hourly space velocity during the startup period is from 40 to 80% of the desired higher final hourly space velocity.

3. A process as claimed in claim 2, wherein the desired final hourly space velocity with charging gas mixture, expressed as the final hourly space velocity of organic precursor compound, is $\geq 80$ l (STP)/l·h.

4. A process as claimed in any of claims 1 to 3, which is for heterogeneously catalyzed gas phase partial oxidation of propene to acrolein and/or acrylic acid.

* * * * *